(12) United States Patent
Akiyama et al.

(10) Patent No.: US 6,410,055 B1
(45) Date of Patent: Jun. 25, 2002

(54) SPHERICAL PHARMACEUTICAL GRANULES COMPRISING MICROCRYSTALLINE CELLULOSE AND A PROCESS FOR THEIR PRODUCTION

(75) Inventors: Hidero Akiyama, Tokyo; Zene Matsumoto; Takashi Ueno, both of Gunma, all of (JP)

(73) Assignee: Novartis International Pharmaceutical Ltd., Hamilton (BM)

( * ) Notice: Subject to any disclaimer, the term of this patent is extended or adjusted under 35 U.S.C. 154(b) by 0 days.

(21) Appl. No.: 09/626,403

(22) Filed: Jul. 26, 2000

Related U.S. Application Data

(62) Division of application No. 09/029,948, filed as application No. PCT/JP96/02504 on Sep. 4, 1996, now Pat. No. 6,242,008.

(30) Foreign Application Priority Data

Sep. 9, 1995 (GB) .............................................. 9518465

(51) Int. Cl.[7] .............................. A61K 9/14; A61K 9/16
(52) U.S. Cl. ......................... 424/490; 424/489; 514/951
(58) Field of Search .............................. 424/489, 499; 514/951

(56) References Cited

U.S. PATENT DOCUMENTS 4,713,245 A * 12/1987 Ando et al.

5,556,639 A * 9/1996 Fielden

FOREIGN PATENT DOCUMENTS

EP          0 608 850        8/1994  ............ A61K/9/16

OTHER PUBLICATIONS

Vertommen et al., *European Journal of Pharmaceutics and Biopharmaceutics*, vol. 40(1), pp. 32–35, (1994).

* cited by examiner

*Primary Examiner*—Gollamudi S. Kishore
*Assistant Examiner*—Brian K. Seidleck
(74) *Attorney, Agent, or Firm*—Thomas R. Savitsky; Susan Hess

(57) ABSTRACT

A high speed agitation granulator method of preparing a substantially spherical granule for pharmaceutical use comprising a medicament for pharmaceutical use, wherein the medicament has an aqueous solubility of 0.01 to 0.30 g/ml, which method comprises introducing a mixture of medicament and excipients comprising at least 5% crystalline cellulose into the granulator and spraying on water or a mixture of ethanol and water as binder solution; a substantially spherical granule for pharmaceutical use comprising famciclovir and 5% or more crystalline cellulose, together with an optional coating; and a sachet containing a unit dose of famciclovir in the form of such granules.

7 Claims, 7 Drawing Sheets

Microscopic Photos of Pyridoxine Spherical Granules
Binder Solution: Water, X5.

|←—1000 μm—→|

Microscopic Photos of Pyridoxine Spherical Granules
Binder Solution: 70% Ethanol, X5.

Microscopic Photos of Pyridoxine Spherical Granules
Concentration of Microcrystalline Cellulose: 20%, X5.

⊢————⊣
1000 μm

Microscopic Photos of Pyridoxine Spherical Granules
Concentration of Microcrystalline Cellulose: 75%, X5.

RELATIONSHIP BETWEEN AMOUNT OF BINDER SOLUTION AND D50%
OF PYRIDOXINE SPHERICAL GRANULES

RELATIONSHIP BETWEEN AGITATION TIME OF BLADE/CROSS SCREW
AND SHAPE FACTOR OF PYRIDOXINE SPHERICAL GRANULES
◇, SF1;   ○, SF2.

Microscopic Photos of Pyridoxine Spherical Granules
Stirring Time: 0 Min, X5.

|← 1000 μm →|

Microscopic Photos of Pyridoxine Spherical Granules
Stirring Time: 14 Min, X5.

Microscopic Photos of Pyridoxine Spherical Granules
Stirring Time: 14 Min, X15.

Microscopic Photos of Pyridoxine Spherical Granules
Stirring Time: 30 Min, X5.

DISSOLUTION CURVE OF PYRIDOXINE SPHERICAL GRANULES

Microscopic Photos of Pyridoxine Spherical Granules after Dissolution Test, X10

SPHERICAL PHARMACEUTICAL GRANULES COMPRISING MICROCRYSTALLINE CELLULOSE AND A PROCESS FOR THEIR PRODUCTION

This is a divisional of application Ser. No. 09/029,948 filed Jul. 7, 1998, now U.S. Pat. No. 6,242,008 which is the 35 USC §371 National Stage entry of PCT International Application No. PCT/JP96/02504, filed Sep. 4, 1996.

FIELD OF THE INVENTION

This invention relates to a method of preparation of granules incorporating a medicament for pharmaceutical use.

BACKGROUND OF THE INVENTION

Granules are a suitable form for medicaments which are to be administered orally. A dose of medicament in the form of granules may be measured and administered by incorporating into a sachet or using a spoon or may be incorporated into a capsule of formulated into a tablet to be swallowed. It is preferred that such granules are of regular shape and substantially spherical to give good fluidity for ease of dispensing and capsule filling or tabletting as well as for aesthetic appeal. Spherical granules are also easier to coat with taste masking, enteric/protective and sustained release coating materials.

At present, there are two methods of preparing spherical granules. One is to extrude a cylindrical granule using a "squeeze-out" type granulation machine and then to make it spherical in shape by using a marumeriser, a machine which "cuts off the edges" of the cylinder shape. This method involves difficult manufacturing conditions and is time consuming which precludes its routine use. The other method used is to gradually coat a core particle such as granulated sugar using a centrifugal flow type granulator but this is a time consuming process and is not generally applicable to a wide range of medicaments where the proportion of the volume of the medicament in the granules high (20% or higher).

The most efficient method of preparing granules is using a high-speed agitation granulator machine which mixes and granulates in one operation using two rotating blades, a main blade with a horizontal plane of rotation and a chopper blade above it with a vertical plane of rotation (cross blade). The medicament and excipients are introduced into the machine in advance and binder solution is then poured or sprayed into the machine from above whilst the blades are rotating. By this method, granules can be prepared quickly and easily but the disadvantage is that the resulting granules are irregular and non-spherical in shape and do not have the advantages associated with spherical granules.

Surprisingly, we have now discovered a method of preparing substantially spherical granules using a high-speed agitation granulator machine thus avoiding the need to use the "squeeze-out" and marumerizer method.

DETAILED DESCRIPTION OF THE INVENTION

Accordingly, the present invention provides a high speed agitation granulator method of preparing a substantially spherical granule for pharmaceutical use comprising a medicament for pharmaceutical use wherein the medicament has an aqueous solubility of 0.01 to 0.30 g/ml, which method comprises introducing a mixture of the medicament and excipients comprising at least 5% crystalline cellulose into the granulator and spraying on water or a mixture of ethanol and water as binder solution.

Suitable medicaments include caffeine which has an aqueous solubility 0.02 g/ml, pyridoxine hydrochloride which has an aqueous solubility of 0.22 g/ml and particularly the orally administered antiviral compounds, famciclovir and acyclovir which have a aqueous solubility of more than 0.25 g/ml. Generally the proportion of medicament with respect to excipients in the composition of the granule is up to 25%, such as up to 5%, 10%, 20%, although it is envisaged that up to 55% medicament could be incorporated.

The mixture of medicament and excipients comprise at least 5% crystalline cellulose, for example up to 10%, 20%, 30%, 40%, 50%, 60%, 70%, 80% and 90%. Other suitable additional excipients include lactose, although the highest yield of spherical granules are when the mixture contains crystalline cellulose as the sole excipient, for example where the composition contains 25% medicament and 75% crystalline cellulose.

The binder solution may be up to 75% ethanol and it is found that the sphericity of granules is higher when the ethanol concentration is higher although from a manufacturing environment point of view and to avoid any problems resulting from residual organic solvent, it may be preferable to use pure water as the binder solution. A linear relationship between the granule size and the amount of binder solution was observed such that the granule size can be regulated by this method (the greater the amount of binder solution, the larger the granule). The granules suitable for administration by spoon are generally more than 500 um in diameter, favourably more than 700 um, up to 1500 um, favourably up to 1000 um. Granules suitable for capsules or tablets are usually smaller than 500 um.

The granules are suitably agitated in the granulator after spraying of the binder solution to improve the spherical shape and smooth the surface of the granules. The agitation time will depend on the size of the granules and composition of the granules, together with the size of the granulator and the speed of rotation of the main blade and the cross blade. The agitation times generally range from 2 to 30 minutes.

The invention provides, in one aspect, a substantially spherical granule for pharmaceutical use comprising famciclovir and 5% or more crystalline cellulose, together with an optional coating. In a preferred aspect the invention provides such a granule comprising famciclovir and crystalline cellulose as the sole excipient, for example a granule containing 25% famciclovir and 75% cellulose.

The following Examples illustrate the process of the invention. The accompanying Figures and Tables illustrate the following with respect to pyridoxine granules:

BRIEF DESCRIPTION OF THE DRAWINGS

FIG. 5 (B-2) shows a photograph of granules taken through a microscope (15) where the agitation time is 14 minutes.

Figure 1A:
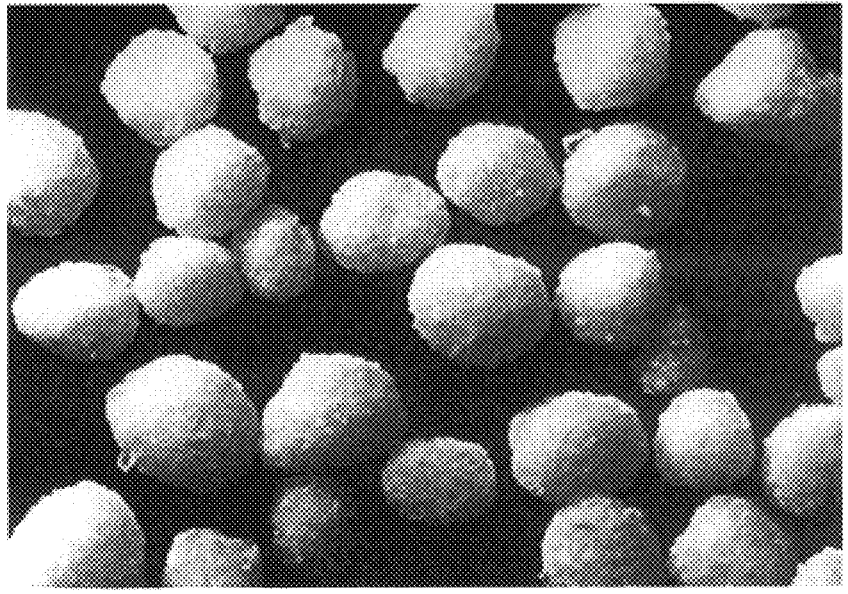
FIG. 1 shows photographs of granules taken through a microscope (×5). (A) is where the binder solution is water and (B) is where the binder solution is 70% ethanol.
Figure 1B:
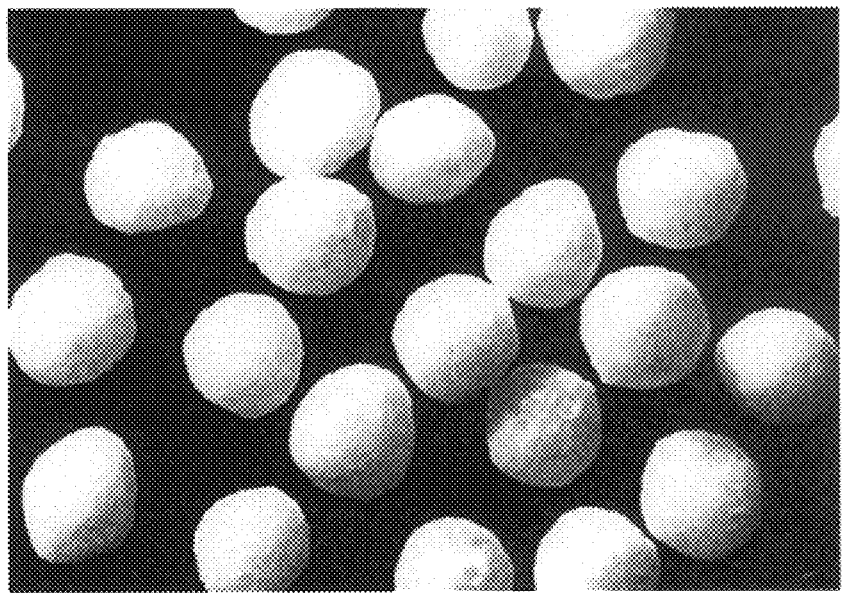
Figure 2A:
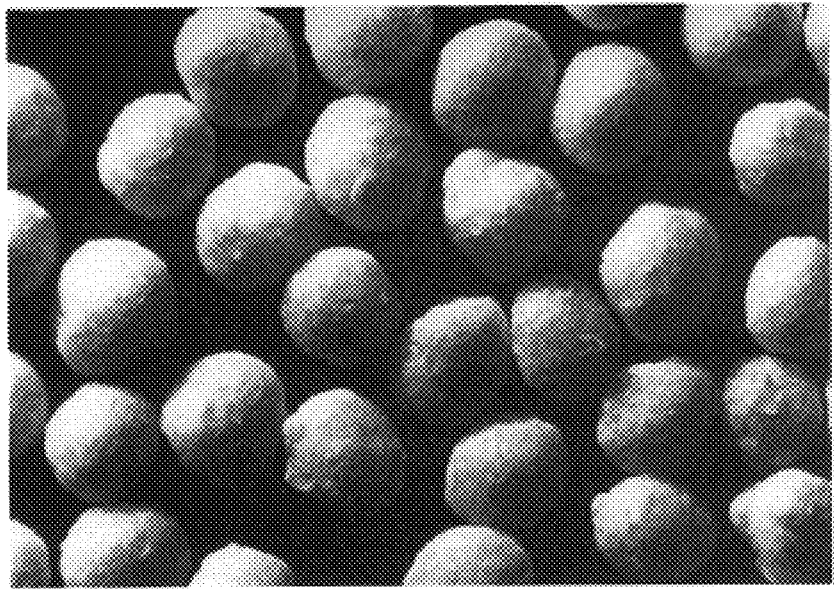
FIG. 2 shows photographs of granules taken through a microscope (×5). (A) is with 20% crystalline cellulose and (B) is with 75% crystalline cellulose.
Figure 2B:
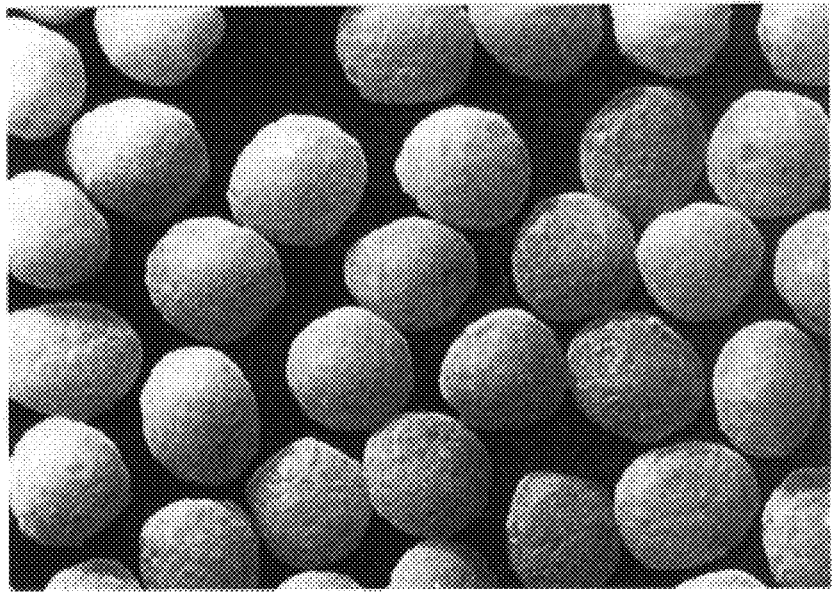
Figure 3:
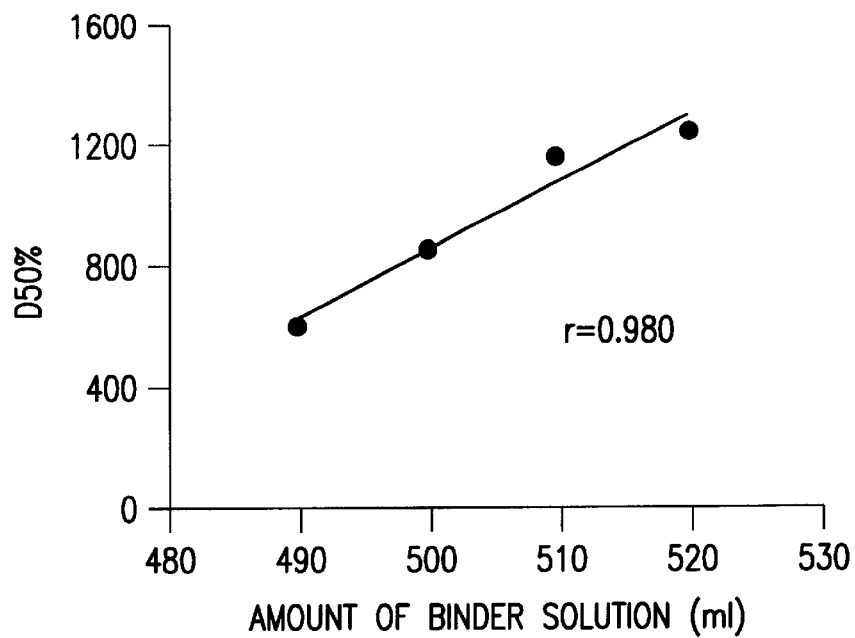
FIG. 3 is a graph showing the relationship between amount of binder solution and the size of granules.
Figure 4:
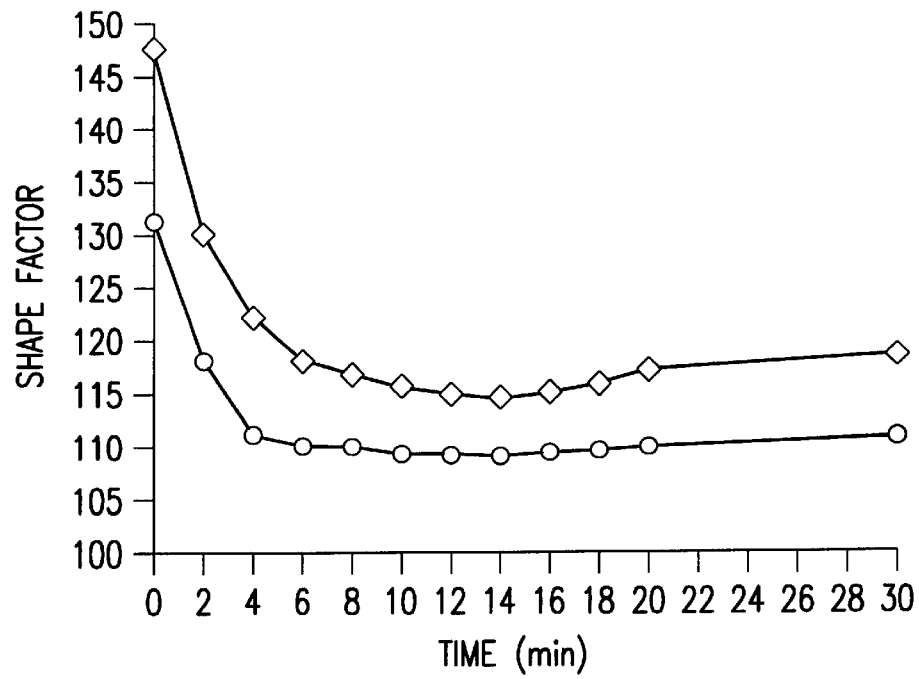
FIG. 4 is a graph showing the relationship between agitation time of the main and cross blades with respect to the shape factor of granules.
Figure 5A:
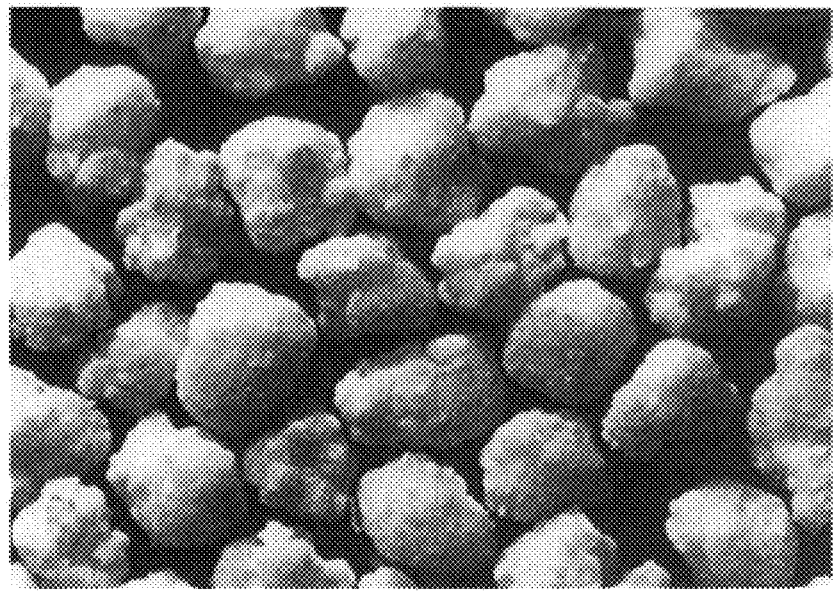
FIG. 5 (A), (B-1), and (C) show photographs of granules taken through a microscope (×5) where agitation times are 0, 14 and 30 minutes respectively.
Figures 1, 5B:
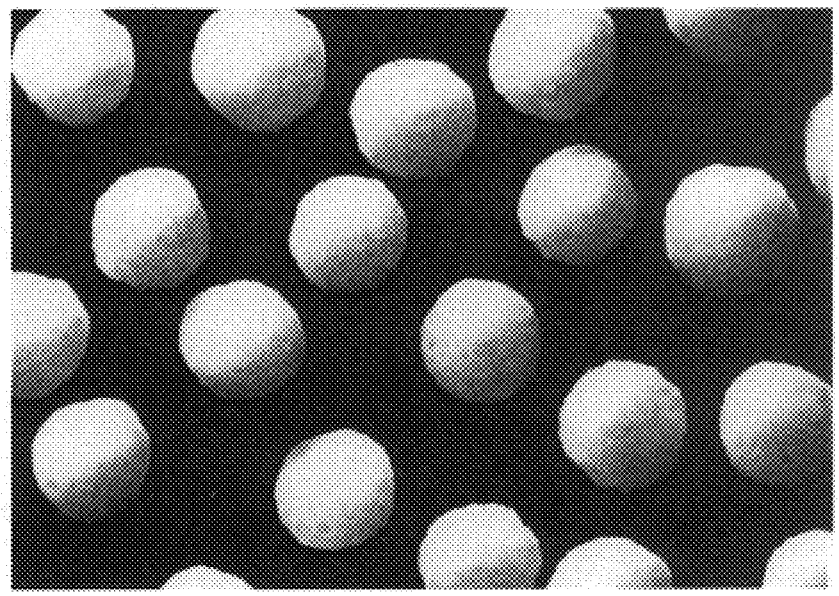
Figures 2, 5B:
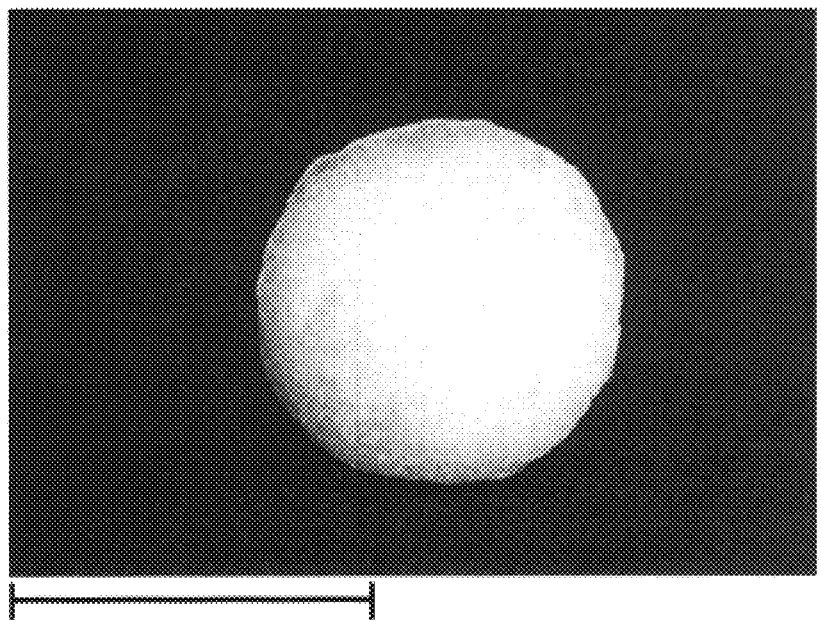
Figure 5C:
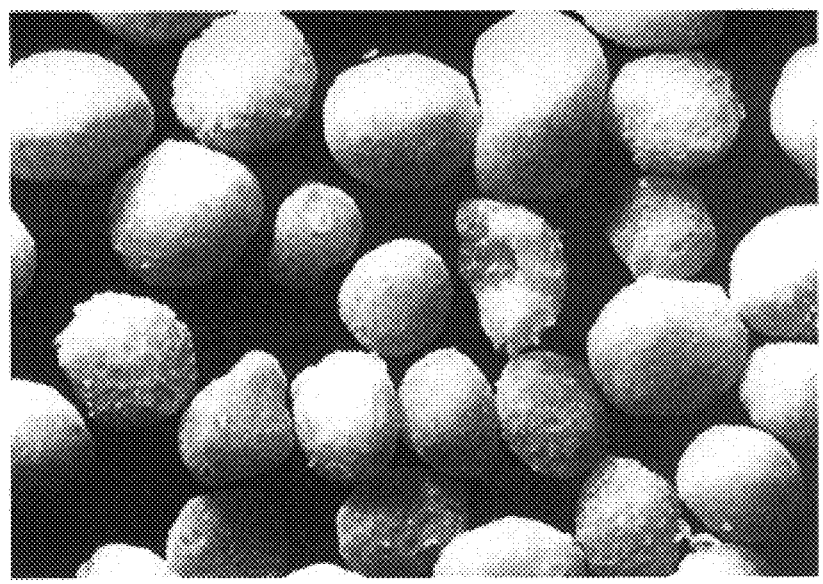
Figure 6:
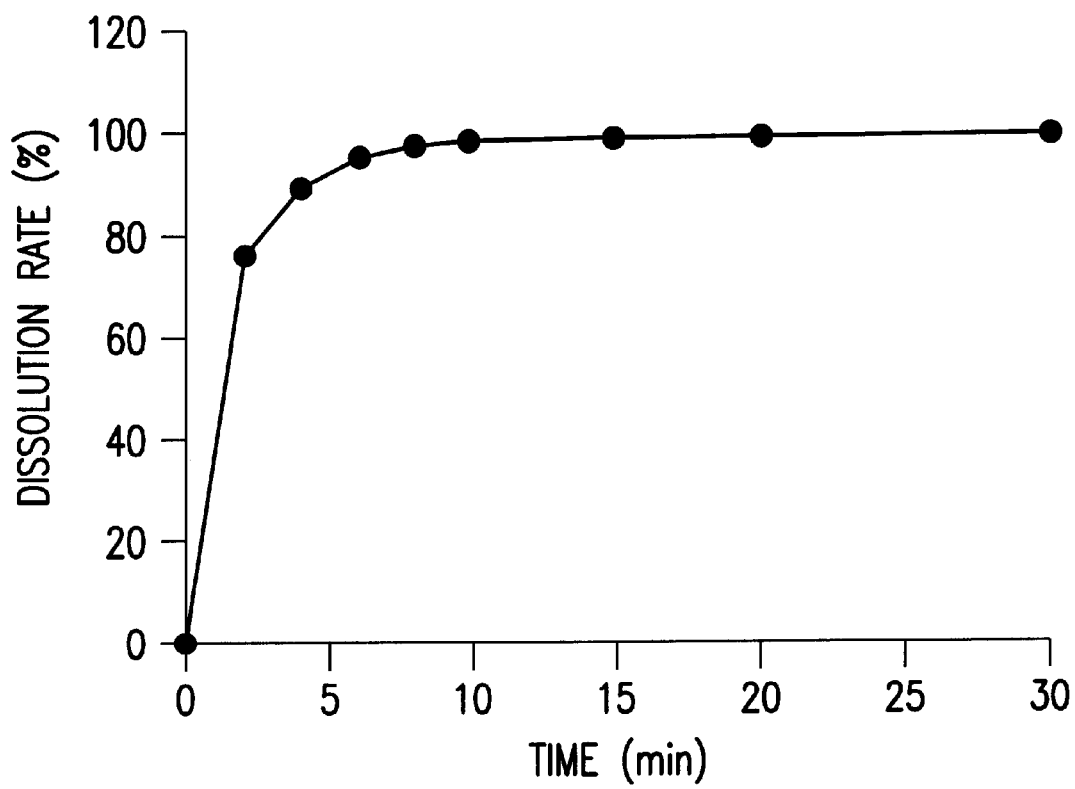
FIG. 6 is a graph shows the dissolution curve of the granules.
Figure 7:
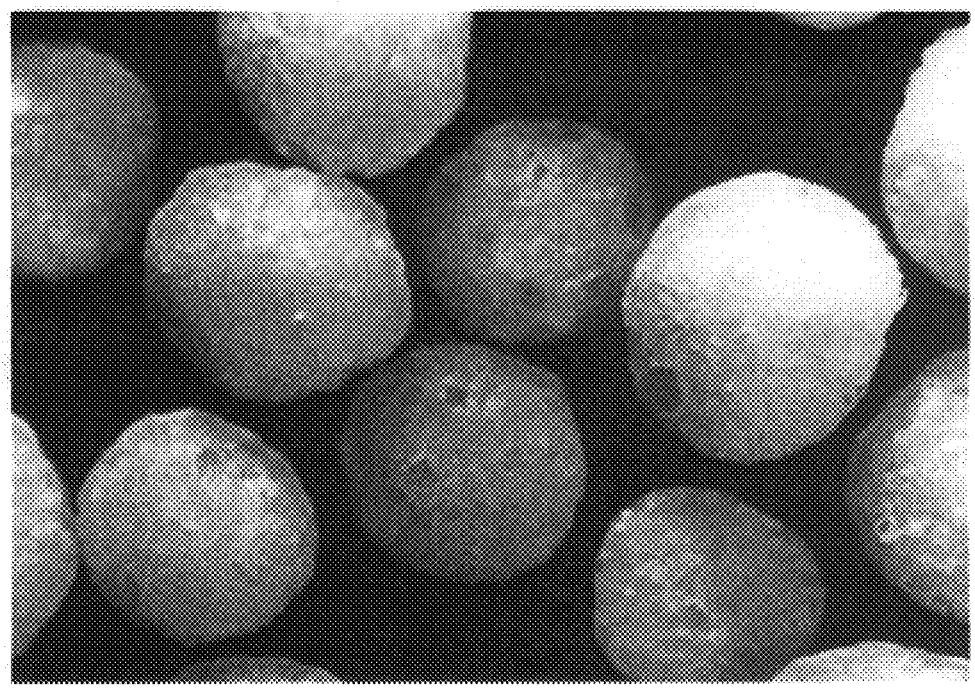
FIG. 7 shows a photograph of granules taken through a microscope (×10) after the dissolution test.

Table I shows the various compositions of the granules with respect to crystalline cellulose content.

Table II shows the effect of ethanol concentration in the binder solution on Shape Factor and yield of granules.

Table III shows the effect of microcrystalline cellulose concentration on Shape Factor and yield of granules.

Table IV shows the effect of amount of binder solution on Particle Size Distribution of 25% pyridoxine granules.

Table V shows the reproducibility of Shape Factor of 25% pyridoxine granules.

Table VI shows the reproducibility of Particle Size Distribution and yield of 25% pyridoxine granules.

EXAMPLES

Preparation Example 1 (10% Caffeine Spherical Granule)

In this example, 700 g of a mixture having the composition shown below were first charged into an agitation granulator (Type VG-5, manufactured by Powlex Corp., Japan) and then 180 ml of 20% ethanol-water solution as a binder liquid were sprayed, at a rate of 100 ml/min, over the mixture in the granulator while rotating the main blade and the cross blade of the granulator at 600 and 3000 rpm, respectively. After the end of spraying, the granulating operation was continued for another two minutes. The resulting grain was then dried at 50° C. for 12 hours using a convection drying oven to obtain the spherical granule.

Composition of the Mixture

| | |
|---|---|
| Caffeine | 10 parts |
| Lactose | 82 parts |
| Crystalline cellulose | 8 parts |

The particle size of this spherical granule obtained was 500–850 um with a yield of 85.5%.

Preparation Example 2 (25% Caffeine Spherical Granule)

In this example, 700 g of a mixture having the composition shown below were first charged into an agitation granulator (Type VG-5, manufactured by Powlex Corp., Japan) and then 370 ml of 70% ethanol-water solution as a binder liquid were sprayed, at a rate of 100 ml/min, over the mixture in the granulator while rotating the main blade and the cross blade of the granulator at 600 and 3000 rpm, respectively. After the end of spraying, the granulating operation was continued for another five minutes while rotating the main blade and the cross blade at 300 and 1000 rpm, respectively. The resulting grain was then dried at 50° C. for 12 hours using a convection drying oven to obtain the spherical granule.

Composition of the Mixture

| | |
|---|---|
| Caffeine | 25 parts |
| Lactose | 55 parts |
| Crystalline cellulose | 20 parts |

The particle size of this spherical granule obtained was 710–1180 um with a yield of 77.7%.

Preparation Example 3 (25% Pyridoxine Hydrochloride Spherical Granule

In this example, 500 g of a mixture having the composition shown below were first charged into an agitation granulator (Type VG-5, manufactured by Powlex Corp., Japan) and then 350 ml of water as a binder liquid were sprayed, at a rate of 100 ml/min, over the mixture in the granulator while rotating the main blade and the cross blade of the granulator at 600 and 3000 rpm, respectively. After completing the spraying, the granulating operation was continued for another 14 minutes while rotating the main blade and the cross blade at 300 and 1000 rpm, respectively. The resulting grain was then dried at 50° C. for 12 hours using a convection drying oven to obtain the spherical granule.

Composition of the Mixture

| | |
|---|---|
| Pyridoxine hydrochloride | 25 parts |
| Crystalline cellulose | 75 parts |

The particle size of this spherical granule obtained was 710–1180 um with a yield of 96.4%.

Preparation Example 4 (25% Famciclovir Spherical Granule)

In this example, 500 g of a mixture having the composition shown below were first charged into an agitation granulator (Type VG-5, manufactured by Powlex Corp., Japan) and then 458 or 459 ml of water as a binder liquid were sprayed, at a rate of 65 ml/min, over the mixture in the granulator while rotating the main blade and the cross blade of the granulator at 600 and 3000 rpm, respectively. After completing the spraying, the granulating operation was continued for another 30 minutes while rotating the main blade and the cross blade at 300 and 1000 rpm, respectively. The resulting grain was then dried at 50° C. for 12 hours using a convection drying oven to obtain the spherical granule.

Composition of the Mixture

| | |
|---|---|
| Famciclovir | 25 parts |
| Crystalline cellulose | 75 parts |

Using 458 ml of binder solution, the particle size of the spherical granule obtained was 600–850 um with a yield of 97.1 percent. Using 459 ml of binder solution, the particle size of the spherical granule obtained was 710–1000 um with a yield of 97.0 percent.

Preparation Example 5 (25% Pyridoxine Hydrochloride Spherical Granule)

In this example, 500 g of a mixture having the composition shown below were first charged into an agitation granulator (Type VG-5, manufactured by Powlex Corp., Japan) and then 326 ml of water as a binder liquid were sprayed, at a rate of 80 ml/min, over the mixture in the granulator while rotating the main blade and the cross blade of the granulator at 600 and 3000 rpm, respectively. After completing the spraying, the granulating operation was continued for another 30 minutes while rotating the main blade and the cross blade at 400 and 2000 rpm, respectively. The resulting grain was then dried at 50° C. for 12 hours using a convection drying oven to obtain the spherical granule.

Composition of the Mixture

| | |
|---|---|
| Pyridoxine hydrochloride | 25 parts |
| Crystalline cellulose | 75 parts |

The particle size of this spherical granule obtained 300–500 um with a yield of 90.7%.

TABLE I

Formulas of Pyridoxine Spherical Granules (%)

| Formulation No. | PSG-1 | PSG-2 | PSG-3 | PSG-4 | PSG-5 | PSG-6 | PSG-7 | PSG-8 |
|---|---|---|---|---|---|---|---|---|
| Pyridoxine hydrochloride | 25 | 25 | 25 | 25 | 25 | 25 | 25 | 25 |
| Microcrystalline cellulose | 10 | 20 | 30 | 40 | 50 | 60 | 70 | 75 |
| Lactose | 65 | 55 | 45 | 35 | 25 | 15 | 5 | 0 |

TABLE II

Effect of Ethanol Concentration in the binder solution on Shape Factor and Yield of Pyridoxine Spherical Granules

| Ethanol concentration (%) | Shape Factor | | Yield (%) |
|---|---|---|---|
| | SF1 | SF2 | |
| 0 | 124.4 | 111.1 | 88.9 |
| 10 | 120.3 | 111.3 | 85.3 |
| 30 | 119.5 | 110.3 | 85.6 |
| 50 | 118.6 | 109.7 | 89.4 |
| 70 | 117.1 | 109.0 | 85.0 |

TABLE III

Effect of microcrystalline Cellulose Concentration on Shape Factor and Yield of Pyridoxine Spherical Granules

| Concentration of microcrystalline cellulose (%) | Shape Factor | | Yield (%) |
|---|---|---|---|
| | SF1 | SF2 | |
| 10 | 120.6 | 111.1 | 70.3 |
| 20 | 119.5 | 109.8 | 79.3 |
| 30 | 119.7 | 110.1 | 83.7 |
| 40 | 119.4 | 109.6 | 84.5 |
| 50 | 119.1 | 111.8 | 88.9 |
| 60 | 117.3 | 109.4 | 94.3 |
| 70 | 115.9 | 109.9 | 95.8 |
| 75 | 115.6 | 109.5 | 96.6 |

TABLE IV

Effect of Amount of Binder Solution on Particle Size Distribution of 25% Pyridoxine Spherical Granules

| Particle size | Amount of binder solution (ml) | | | |
|---|---|---|---|---|
| (μm) | 490 | 500 | 510 | 520 |
| 1400–1700 | 0.3% | 0.5% | 0.9% | 1.5% |
| 1180–1400 | 0.5 | 1.5 | 49.0 | 82.4 |
| 1000–1180 | 1.1 | 11.9 | 42.5 | 12.3 |
| 850–1000 | 1.9 | 74.0 | 5.9 | 2.5 |
| 710–850 | 7.5 | 10.6 | 1.1 | 0.6 |
| 500–710 | 87.7 | 1.3 | 0.4 | 0.3 |
| 355–500 | 0.8 | 0.1 | 0.1 | 0.1 |
| 0–355 | 0.2 | 0.1 | 0.1 | 0.3 |
| D 50% | 617 μm | 875 μm | 1180 μm | 1270 μm |

TABLE V

Reproducibility of Shape Factor of 25% Pyridoxine Spherical Granules

| Repetition No. | SF1 | SF2 |
|---|---|---|
| 1 | 114.1 | 108.2 |
| 2 | 114.3 | 108.0 |
| 3 | 114.2 | 107.9 |
| 4 | 114.4 | 108.2 |

TABLE VI

Reproducibility of Particle Size Distribution and Yield of 25% Pyridoxine Spherical Granules

| Particle size | Repetition No. | | | |
|---|---|---|---|---|
| (μm) | No. 1 | No. 2 | No. 3 | No. 4 |
| 1400–1700 | 0.9 | 0.2 | 0.2 | 0.4 |
| 1180–1400 | 1.8 | 1.0 | 1.0 | 1.6 |
| 1000–1180 | 5.8 | 4.1 | 3.4 | 3.5 |
| 850–1000 | 61.7 | 67.4 | 61.5 | 66.3 |
| 710–850 | 27.7 | 24.9 | 30.8 | 25.7 |
| 500–710 | 2.1 | 2.1 | 2.9 | 2.1 |
| 355–500 | 0.0 | 0.2 | 0.1 | 0.4 |
| 0–355 | 0.0 | 0.0 | 0.1 | 0.0 |
| Yield (710–1180) | 95.2 | 96.4 | 95.7 | 95.5 |

What is claimed is:

1. A method of preparing substantially spherical granules of caffeine or acyclovir for pharmaceutical use, which method comprises introducing a mixture consisting essentially of approximately 25% caffeine or acyclovir and 75% microcrystalline cellulose as the sole excipient into a high speed agitation granulator and spraying on water or a mixture of ethanol and water as a binder solution.

2. A method according to claim 1 where the amount of binder solution is regulated such that granules are more suitable for administration by spoon and are generally more than 500 um in diameter.

3. A method according to claim 1 wherein the granules are agitated in the granulator after spraying of the binder solution to improve the spherical shape and smooth the surface of the granules.

4. A substantially spherical granule for pharmaceutical use produced according to the method of claim 1 comprising caffeine, pyridoxine hydrochloride or acyclovir and at least 5% microcrystalline cellulose as the sole excipient together with an optional coating.

5. A sachet containing a unit dose of caffeine, pyridoxine hydrochloride or acyclovir in the form of granules according to claim 4.

6. A method according to claim 1 wherein the granule has a diameter of 500 to 1500 um.

7. A method according to claim 1 wherein the granule comprises acyclovir and at least 5% microcrystalline cellulose and an optional coating.

* * * * *